United States Patent [19]

Behnke, Jr. et al.

[11] Patent Number: 4,502,876
[45] Date of Patent: Mar. 5, 1985

[54] CARTRIDGE FOR USE IN REBREATHING APPARATUS

[76] Inventors: Albert R. Behnke, Jr., 2241 Sacramento St., San Francisco, Calif. 94115; John P. Jones, Jr., 5106 Hill Rd., Lake Medical Building, Lakeport, Calif. 95453; Charles E. Michielsen, deceased, late of Pacifica, Calif.; by Sophie Michielsen, legal representative, Pacifica, Calif. 94044

[21] Appl. No.: 567,683

[22] Filed: Jan. 3, 1984

[51] Int. Cl.³ .............................................. B01D 53/04
[52] U.S. Cl. ......................................... 55/387; 55/516
[58] Field of Search ......... 55/316, 387, 516, DIG. 17, 55/DIG. 25; 422/211, 218, 221

[56] References Cited

U.S. PATENT DOCUMENTS

| | | | |
|---|---|---|---|
| 680,813 | 8/1901 | Simonini | 422/211 X |
| 1,328,058 | 1/1920 | Ryan | 55/387 |
| 3,047,370 | 7/1962 | Avtges et al. | 55/316 X |
| 3,240,567 | 3/1966 | Caparreli et al. | 55/387 X |
| 3,507,621 | 4/1970 | Goodman et al. | 422/211 X |
| 3,616,617 | 11/1971 | DeGroote | 55/DIG. 25 |
| 3,820,959 | 6/1974 | Wise et al. | 422/211 |
| 4,177,048 | 12/1979 | Rivers et al. | 55/387 X |
| 4,266,539 | 5/1981 | Parker et al. | 55/387 X |
| 4,367,079 | 1/1983 | Wallsten | 55/387 X |

FOREIGN PATENT DOCUMENTS

| | | | |
|---|---|---|---|
| 2063095 | 6/1981 | United Kingdom | 55/387 |
| 186974 | 10/1966 | U.S.S.R. | 55/387 |

*Primary Examiner*—Robert Spitzer
*Attorney, Agent, or Firm*—Ernest M. Anderson

[57] ABSTRACT

A cartridge for use in rebreathing apparatus comprising a filtering device for removing carbon dioxide, a pair of flexible containers (one disposed within the other and in fluid communication with each other through a restricted opening), a coaxial connector for fluidly connecting the cartridge to a rebreathing apparatus, means for maintaining a separation between the pair of flexible connectors and a metallic shield disposed in the flow path of exhaled gases for removing moisture.

9 Claims, 4 Drawing Figures

CARTRIDGE FOR USE IN REBREATHING APPARATUS

SUMMARY OF THE INVENTION

A cartridge is disclosed for use in rebreathing apparatus which includes a filtering device for removing carbon dioxide. In brief, the cartridge comprises a pair of flexible containers one disposed within the other and in fluid communication with each other through a restricted opening. A filter containing $CO_2$ absorbent is disposed within the innermost container, said filter and outermost container being connected by fluid passages for passing exhaled gas through said filter and withdrawing filtered gas from the outermost container. The pair of flexible containers increase the retention time for processing exhaled gases for rebreathing, thereby enhancing the removal of moisture and cooling of the exhaled gases.

The invention further comprises a replaceable cartridge having a pair of coaxial connectors, one connector extending through the other and being in fluid communication with the filter, the other connector being in fluid communication with the outermost flexible container. In addition, the cartridge comprises a metallic shield disposed in the flow path of exhaled gas passing from the filter into the innermost flexible container, said shield serving as a heat exchanger that condenses moisture carried in the exhaled gases.

A principal object of the present invention is, therefore, to provide an improved cartridge for rebreathing apparatus, a cartridge that may be quickly and easily replaced when the $CO_2$ absorbent is spent.

Another object is to provide a replaceable cartridge for rebreathing apparatus having a pair of flexible containers one disposed within the other and yet in fluid communication through a restricted opening, said containers serving to increase the retention time for processing exhaled gases to enhance cooling and the removal of moisture.

A still further object of the invention is to provide a replaceable cartridge of the kind described having a metallic shield disposed in the flow path of exhaled gases passing from the filter into a flexible container, said shield serving to condense moisture from exhaled gases.

And yet a further object is to provide a replaceable cartridge of the kind described and a pair of coaxial connectors which allow the cartridge to be rapidly disconnected from a rebreathing apparatus and substituted with another.

Other objects of the invention will become apparent in view of the following detailed description.

BRIEF DESCRIPTION OF THE DRAWINGS

In the drawings forming a part of this application and in which like parts are identified by like reference numerals.

DETAILED DESCRIPTION OF THE INVENTION

Figure 1:
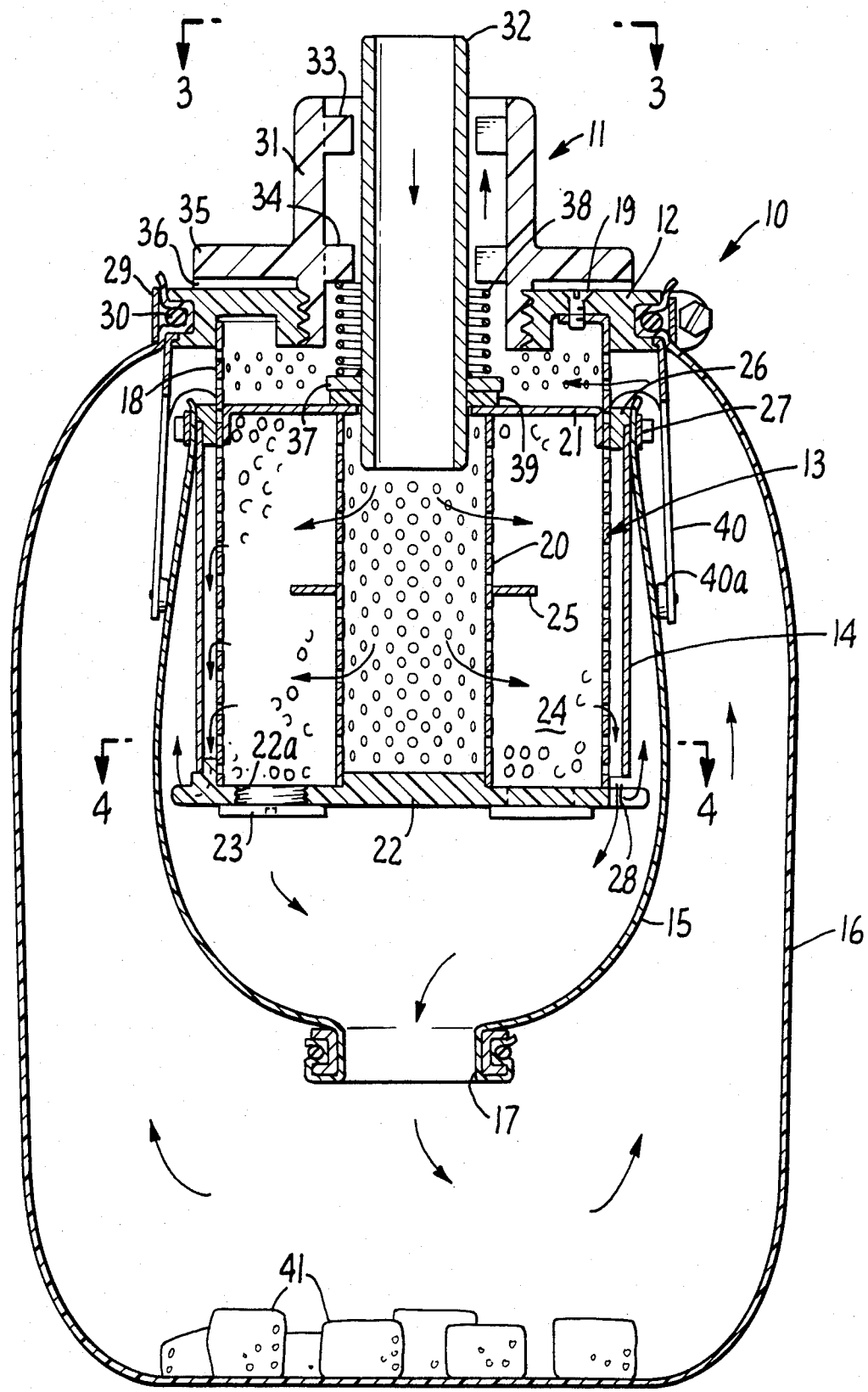
FIG. 1 is a longitudinal section of a preferred embodiment of the invention in a replaceable cartridge for rebreathing apparatus.

Referring to FIG. 1 in particular, there is shown a preferred embodiment of the invention in a cartridge 10 that connects to a rebreathing apparatus (not shown) by means of a pair of coaxial connectors 11. Cartridge 10 essentially comprises a mounting flange 12, a filter cartridge 13, a metallic condenser plate 14 and a pair of flexible containers 15 and 16, container 15 being disposed within container 16 and being in fluid communication therewith through a restricted opening 17.

Filter 13 comprises a perforated cylindrical sleeve 18 that mounts to flange 12 by means of a plurality of screws 19. A perforated cylindrical core 20 is disposed coaxially within sleeve 18 and is mounted between a pair of end walls 21 and 22. The upper end wall 21 is disposed within the upper end of perforated sleeve 18, said wall being formed with a central opening through which one portion or member of the coaxial connector 11 is received. The lower end wall 22 closes off the lower end of the perforated sleeve 18 and core 20. A pair of threaded openings 22a are formed in end wall 22 for the purpose of inserting discrete particles of $CO_2$ absorbent material 24. The openings are then sealed by the use of plugs 23. Filter 13 is preferably formed with one or more interior baffles 25 to inhibit channeling and direct a lateral flow of gases as they pass into and through perforated core 20 and spread laterally outward as shown by arrows.

Flexible container 15 essentially encloses filter 13 the upper end thereof being peripherally connected to a spacer ring 26 mounted near but spaced from the upper end of perforated sleeve 18. Container 15 is secured to the spacer ring by means of a clamping band 27.

Figure 2:
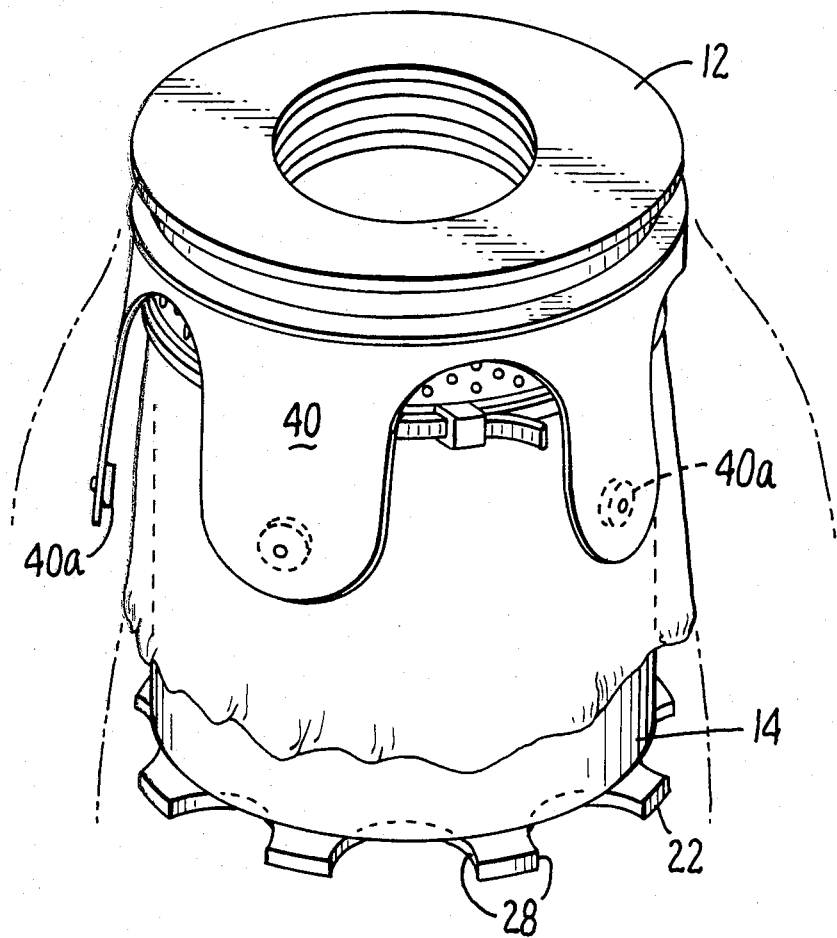
FIG. 2 is a perspective view of a portion of the cartridge.
Figure 3:
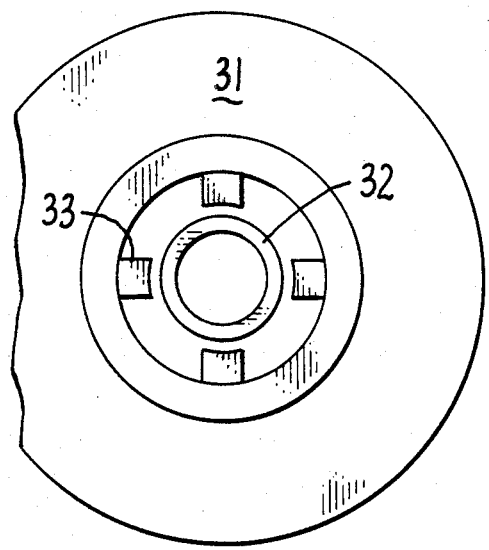
FIG. 3 is a top plan view of a portion of the cartridge as shown on lines 3—3 of FIG. 1.
Figure 4:
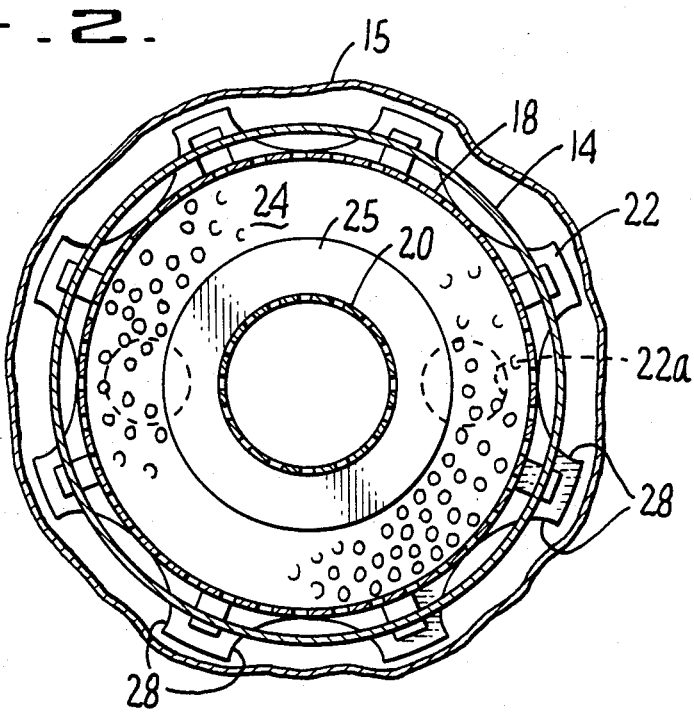
FIG. 4 is a section taken on lines 4—4 of FIG. 1.

Metallic condenser plate 14 is supported between the spacer ring 26 and the lower end wall 22. Plate 14 encircles the perforated sleeve 18 but in spaced relationship thereto, thus providing a cylindrical air space for the passage of gases downward toward the end plate. A series of arcuate openings 28 (see FIGS. 2 and 4) allow the passage of gases into container 15. The flexibility of the container permits it to expand or contract independently of container 16 as gases are received therein or removed through restricted opening 17.

Flexible container 16 is secured to mounting flange 12 by means of an upper band or clamp 29 and a resilient O-ring 30 set within a groove formed peripherally of the flange.

Connector 11 essentially comprises a two piece assembly, a first connector member 31 threadably connected to flange 12 and a tubular member 32 centered within an opening formed in the first member 31 by upper and lower standoffs 33 and 34. A collar 35 radially formed on member 31 compresses a gasket 36 upon threaded engagement of member 31 with flange 12.

Tubular member 32 is similarly provided with a flange 37. A helical spring 38 disposed between flange 37 and the lower standoff 34 resiliently forces flange 37 against a gasket 39 as connector member 31 is threadably engaged with mounting flange 12.

In the preferred embodiment shown means is further provided for maintaining a separation between flexible containers 15 and 16 on either side of spacer ring 26. This function is performed by a skirt 40 formed with depending ears that carry standoff buttons 40a. Skirt 40 serves the purpose of maintaining open fluid communication of processed gas as it moves upward between inner container 15 and outer container 16 and particularly as it is withdrawn through the perforations of sleeve 18 in the region above upper wall 21 and flange 12.

In operation, cartridge 10 is adapted for use with rebreathing apparatus having a coaxial line of fluid communication. Exhaled gases pass into tubular member 32, into and through perforated core 20 and the $CO_2$ absorbent 24, and out through perforations of sleeve 18. The gases then flow between the metallic condenser plate 14 and the perforated sleeve, passing downward through the lower openings formed in the lower end wall 22 and into the inner flexible container 15. The restricted opening 17 limits the rate at which the gases may be expelled into outer container 16. This allows the flexible container to expand independently of the outer container, such gases passing upward between the inner flexible container and the outer surface of the metallic plate. This enhances cooling of the gases and the removal of moisture as condensate upon the surfaces of plate 14. Such moisture then gravitates downward through the restricted opening 17 where it is collected by absorbent material such as sponges 41 loosely disposed in the bottom of outer container 16.

Although a preferred embodiment of the invention has been illustrated and described, various modifications and changes may be resorted to without departing from the the spirit of the invention or the scope of the appended claims and each of such modifications and changes is contemplated.

What is claimed is:

1. A cartridge for use in rebreathing apparatus comprising: a first flexible container; a second flexible container disposed within said first and in fluid communication therewith through a restricted opening; a filter containing $CO_2$ absorbent within said second flexible container; first conduit means for passing exhaled gas through said filter and into said second container; and second conduit means for withdrawing gas from said first flexible container; whereby $CO_2$ is removed from exhaled gases passing through said filter, said first and second flexible containers increasing the retention time for processing exhaled gases for rebreathing to enhance cooling and moisture removal.

2. The cartridge of claim 1, said first and second conduit means comprising a pair of tubular coaxial connectors, one connector extending through the other and being in fluid communication with said filter, the other connector being in fluid communication with said first flexible container.

3. The cartridge of claim 1, and further comprising a metallic shield disposed in the flow path of exhaled gas passing from said filter into said second flexible container.

4. The cartridge of claim 1, and further comprising moisture absorbent material within said first flexible container.

5. The cartridge of claim 1, and further comprising baffle members within said filter for directing exhaled gases through different portions of $CO_2$ absorbent.

6. A replaceable cartridge for use in rebreathing apparatus comprising: a mounting flange having an opening therethrough; a first flexible container mounted to said flange peripherally of said opening; a perforated sleeve mounted to said flange within said first flexible container; a perforated core mounted within said perforated sleeve; a pair of end walls, an upper end wall mounted within the upper end of said sleeve and having a central opening in fluid communication with the upper end of said perforated core, the other end wall closing off the lower end of said sleeve and said core; discrete particles of $CO_2$ absorbent material disposed within the space defined by the interior surface of said sleeve, the exterior surface of said core and between said pair of end walls; a metallic shield disposed about said perforated sleeve and in spaced relation thereto; a second flexible container disposed within said first flexible container, the upper end thereof being connected to the upper end wall of said filter, the lower end being in fluid communication with the first flexible container through a restricted opening, said second flexible container substantially enclosing said filter and capable of expanding and contracting independently of said first flexible container.

7. The replaceable cartridge of claim 6 and further comprising a coaxial connector sealingly engageable with said flange, said connector having a first passageway fluidly connected with said filter core through said upper end plate and a second passageway coaxial relative to said first passageway and fluidly connected with said first flexible container through said perforated sleeve above said upper end wall.

8. The replaceable cartridge of claim 7, said coaxial connector comprising a first connector member threadably connected to said flange and having an opening therethrough in fluid communication with the upper end of said perforated sleeve above said upper end wall; a tubular connector member mounted within the opening of said first connector member, one end thereof being received through the central opening of said upper end wall and defining said first passageway, the opening through said first connector member and the exterior surface of said tubular connector member defining said second passageway.

9. The replaceable cartridge of claim 6 and further comprising means for maintaining a separation between said first and second flexible containers to allow the passage of gases from said first flexible container through said perforated sleeve above said upper end wall.

* * * * *